United States Patent [19]

DeLuca et al.

[11] Patent Number: 4,927,815
[45] Date of Patent: May 22, 1990

[54] COMPOUNDS EFFECTIVE IN INDUCING CELL DIFFERENTIATION AND PROCESS FOR PREPARING SAME

[75] Inventors: Hector F. DeLuca, Deerfield; Heinrich K. Schnoes; Kato L. Perlman, both of Madison, all of Wis.; Andrzej Kutner, Warsaw, Poland

[73] Assignee: Wisconsin Alumni Research Foundation, Madison, Wis.

[21] Appl. No.: 187,680

[22] Filed: Apr. 29, 1988

[51] Int. Cl.$^5$ ............................ A61K 31/59; C07J 9/00
[52] U.S. Cl. .................................. 514/167; 552/653; 552/505; 552/555
[58] Field of Search ...................... 260/397.2; 514/167

[56] References Cited

U.S. PATENT DOCUMENTS

| | | | |
|---|---|---|---|
| 4,717,721 | 1/1988 | DeLuca et al. | 514/167 |
| 4,758,382 | 7/1988 | Sterling et al. | 260/397.2 |
| 4,804,502 | 2/1989 | Baggiolini et al. | 260/397.2 |

OTHER PUBLICATIONS

Chemical Abstracts; vol. 109 (1988), #55060u; Kutner et al.
1,2,5-Dihydroxyvitamin D$_3$Analogs and Cell Differentiation; University of Wisconsin-Madison, Dept. of Biochemistry (1989); DeLuca et al.

*Primary Examiner*—Joseph A. Lipovsky
*Attorney, Agent, or Firm*—Andrus, Sceales, Starke & Sawall

[57] ABSTRACT

This invention provides novel side chain homologs of 1α,25-dihydroxyvitamin D$_3$ which exhibit enhanced and highly selective activity in inducing differentiation of malignant cells. It also provides a general method of synthesis applicable to the preparation of a variety of vitamin D side chain analogs, and a method of treatment of neoplastic diseases which takes advantage of the selective differentiation activity of the new vitamin D homologs.

26 Claims, 4 Drawing Sheets

Process Scheme I
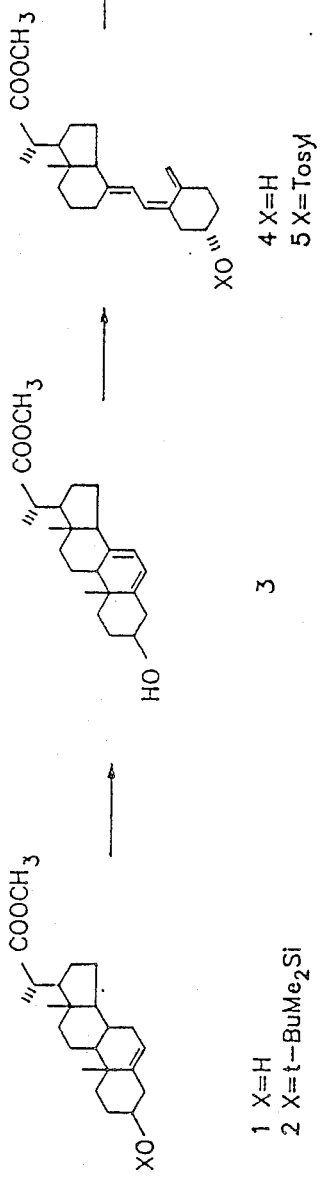
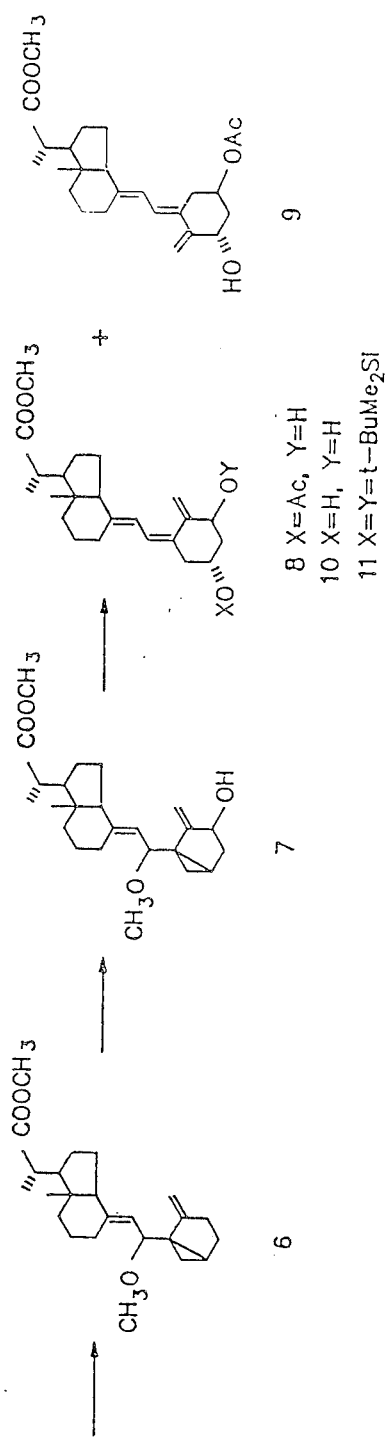

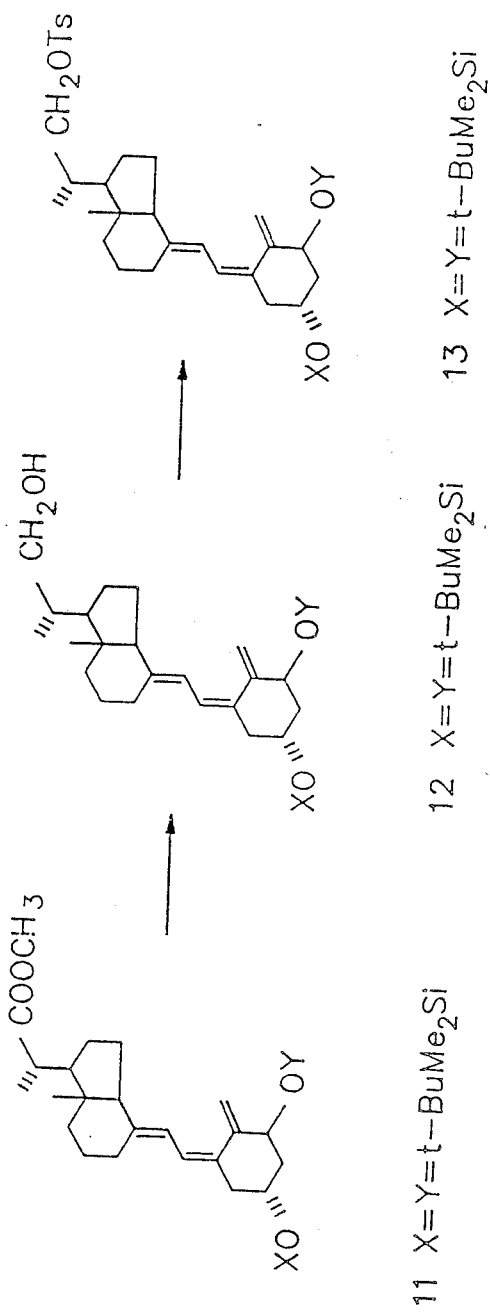

Process Scheme III
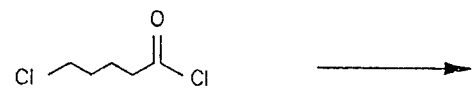
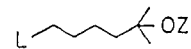
- 15   L=Cl, Z=H
- 16   L=PhS, Z=H
- 17   L=PhSO$_2$, Z=H
- 18   L=PhSO$_2$, Z=SiEt$_3$
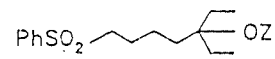
19
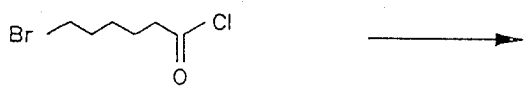
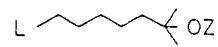
- 21   L=Br, Z=H
- 22   L=PhSO$_2$, Z=H
- 23   L=PhSO$_2$, Z=SiEt$_3$
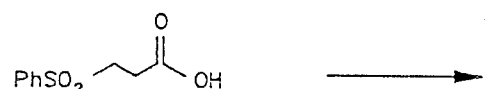
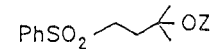
- 25   Z=H
- 26   Z=SiEt$_3$
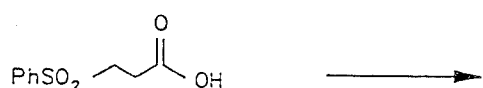
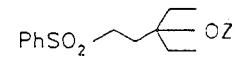
- 27   Z=H
- 28   Z=SiEt$_3$

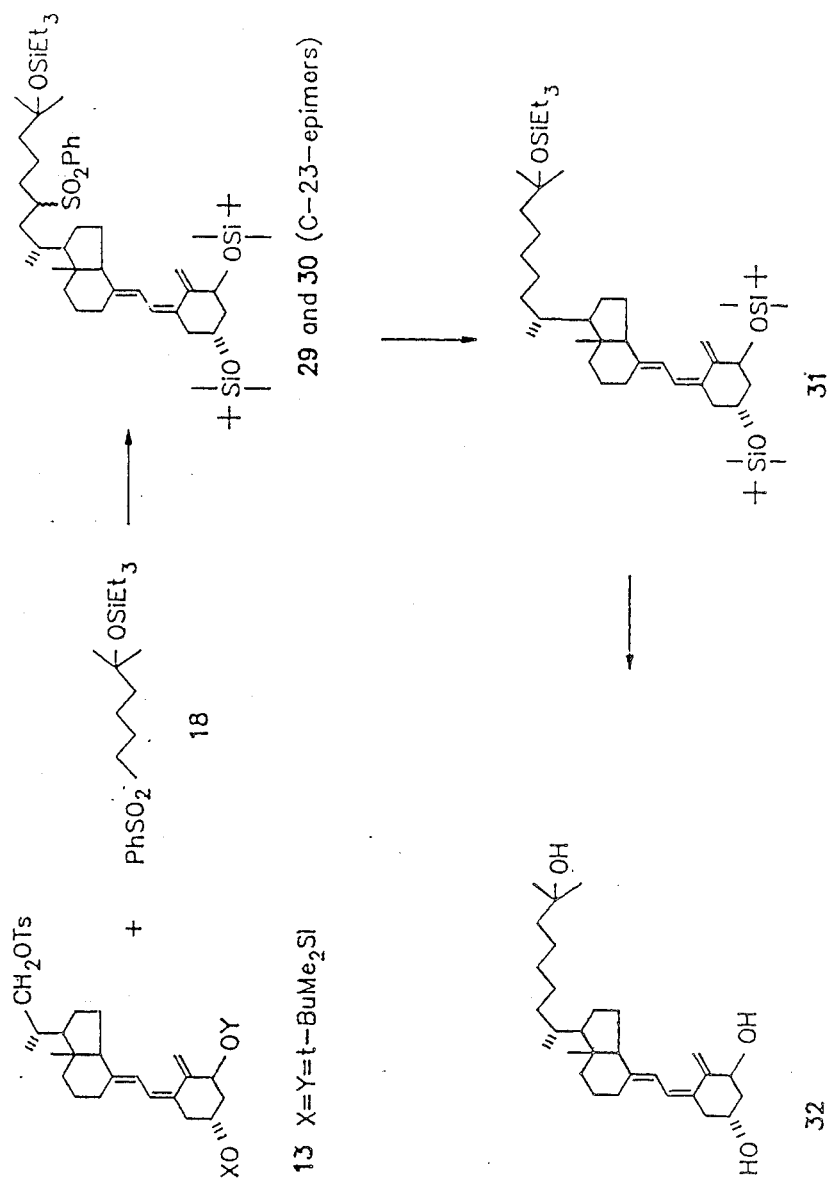

COMPOUNDS EFFECTIVE IN INDUCING CELL DIFFERENTIATION AND PROCESS FOR PREPARING SAME

This invention was made in the course of work supported by grants or awards from the Department of Health and Human Services. The Government has certain rights in this invention.

This invention relates to novel vitamin D compounds and to a general process for their preparation. More specifically, the invention concerns 1α-hydroxyvitamin D side chain homologs, which are specifically and unexpectedly active in differentiating malignant cells, and to methods of use of the new compounds for the treatment of neoplastic diseases, including specifically leukemoid diseases.

BACKGROUND

The compounds of the vitamin D series are well known as agents essential for controlling calcium homeostasis in the animal or human. It is also known that it is not vitamin D itself, but metabolites generated from it in the animal or human body, that are effective in regulating calcium metabolism. In this context, the most important vitamin D metabolite is 1α,25-dihydroxyvitamin $D_3$ (1,25-$(OH)_2D_3$). This compound, as well as certain structural analogs, such as 1α-hydroxyvitamin $D_3$ (1α-OH-$D_3$), 1α-hydroxyvitamin $D_2$ (1α-OH-$D_2$), or certain fluorine substituted 1,25-$(OH)_2D_3$ derivatives, are highly potent in stimulating intestinal calcium absorption, as well as the resorption of calcium from bone (bone mobilization). As a consequence, these compounds are now used, or have been proposed for use, as pharmaceutical agents for the treatment of a variety of calcium metabolism disorders, such as renal osteodystrophy, hypoparathyroidism, vitamin D-resistant rickets, or osteoporosis.

More recent research has established that 1,25-$(OH)_2D_3$, in addition to its role in regulating calcium homeostasis in vivo, also expresses other biological functions. Specifically, it has been shown that 1,25-$(OH)_2D_3$, and compounds closely related to it (e.g. 1α-OH-$D_3$, or fluoro analogs of 1,25-$(OH)_2D_3$) are highly potent in inducing cell differentiation. Most importantly, it has been found that 1,25-$(OH)_2D_3$ will inhibit the proliferation of malignant cells (specifically, leukemia cells) and bring about their differentiation, in culture, to normal monocytes [Abe, et al., Proc. Natl. Acad. Sci. USA 78, 4990 (1981); Honma et al., ibid, 80, 201 (1983)]. Because of this remarkable activity, 1,25-$(OH)_2D_3$ and related compounds have been proposed as anticancer, specifically antileukemic, agents (Suda et al., U.S. Pat. No. 4,391,802). However, even though these compounds are, indeed, highly effective in differentiating malignant cells in culture, their practical use in differentiation therapy as anticancer agents is severely limited because of their equally high potency as agents affecting cancer metabolism. At the levels required in vivo for effective use as antileukemic agents, these same compounds can induce markedly elevated and potentially dangerous blood calcium levels by virtue of their inherent calcemic activity. This calcemic activity precludes, or severely limits, the use of these known vitamin D compounds in the treatment of malignancies, and indicates a need for compounds with greater specificity and selectivity of action.

In this disclosure the terms 'calcemic activity' or 'calcemic action' are intended as a short-hand designation of the well-known ability of vitamin D compounds to raise blood calcium levels by virtue of their stimulation of intestinal calcium absorption (Ca transport) and of calcium resorption from bone (bone mobilization). The term 'differentiation activity' refers to the more recently discovered activity of certain vitamin D compounds in arresting the proliferation of malignant cells and inducing their differentiation to normal cells.

Previous work has led to the preparation of several compounds with enhanced differentiation activity. Thus, U.S. Pat. No. 4,717,721, as well as other publications [Ostrem & DeLuca, Steroids, 49 73–102 (1988); Ostrem et al., J. Biol. Chem. 262, 14164 (1987)] disclose that 1,25-$(OH)_2D$ analogs in which the side chain is elongated by one carbon, exhibit a differentiation activity for leukemia cells about ten times greater than 1,25-$(OH)_2D_3$ itself. However, such compounds still are approximately as potent as 1,25-$(OH)_2D_3$ in stimulating calcium absorption and elevating serum calcium levels, and thus do not overcome the problem of the undesired potent 'calcemic action' discussed above. Thus, although such compounds show an improved differentiation/calcemic activity ratio, they are not selective in that their calcemic potency is as high as that of the parent compound (1,25-$(OH)_2D_3$). Other vitamin D-related compounds, which are said to exhibit preferential differentiation activity, have been reported [Ostrem et al., supra; Kubodera et al. Chem. Pharm. Bull. 34, 2286–89 (1986); Ikekawa et al. Chem. Pharm. Bull. 35, 4362 (1987)], but these are structurally distinct and different from the compounds of the present invention.

BRIEF DESCRIPTION OF THE DRAWINGS

Process schemes I–IV show the synthetic routes utilized in the specification to produce the compounds of the instant claims.

SUMMARY OF THE INVENTION

The present invention provides a novel class of compounds exhibiting a desired, and highly advantageous, pattern of biological activity. These compounds are characterized by a high potency (compared to that of 1,25-$(OH)_2D_3$) in inducing the differentiation of malignant cells, while exhibiting much lower activity than 1,25-$(OH)_2D_3$ in their effect on calcium metabolism. Hence, these compounds are highly specific differentiation agents, and their activity pattern would allow their use in differentiation therapies of malignancies. Their very high differentiation activity combined with their markedly reduced or abolished action on calcium metabolism allows the in vivo administration of these compounds for the treatment of malignancies without inducing excessively elevated blood calcium levels. Because of such characteristics, they would be the preferred therapeutic agents for such purposes.

Structurally, the key feature of the compounds having these desirable biological attributes is that they are side chain homologs of 1,25-$(OH)_2D_3$ in which the side chain is elongated by insertion of two or three methylene units into the chain. Thus, the compounds of this type are characterized by the following general structure:

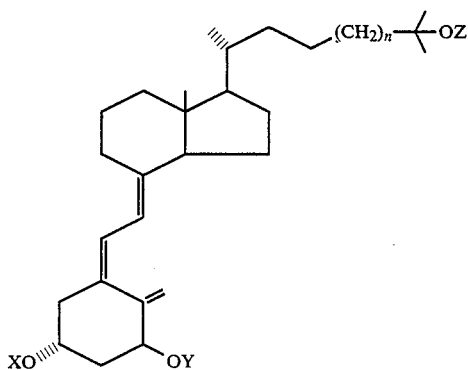

where X, Y and Z, which may be the same or different, represent hydrogen or a hydroxy-protecting group, and where n is an integer having the values 3 or 4.

24-Dihomo-1,25-$(OH)_2D_3$ and its hydroxy-protected derivatives, that is the compounds having the structure shown above, where n is 3 and 24-trihomo-1,25-$(OH)_2D_3$ and its hydroxy-protected derivatives, i.e. the compounds as shown above where n=4 are preferred examples of the structurally defined compounds above.

The compounds of this invention are related to the 24-homo-vitamin D compound of U.S. Pat. No. 4,717,721. However, the compounds of this invention can be distinguished by both structural and biological characteristics. Structurally, the compounds are novel vitamin D homologs with the key characteristic that the side chain is extended by insertion of two or three methylene units into the carbon chain, and biologically, the compounds are highly selective cell differentiation agents with a potency at least similar to or greater than that of 1,25-$(OH)_2D_3$ in inhibiting the proliferation and inducing the differentiation of malignant cells, while exhibiting no, or greatly reduced, calcemic activity.

The present invention, therefore, provides novel compounds specifically useful for promoting the differentiation of malignant cells, and for the treatment of neoplastic diseases.

This invention also provides a new method for the preparation of vitamin D compounds. This method can be used for the synthesis of the new compounds shown above, as well as for the synthesis of known vitamin D metabolites or other homologs, or other side-chain modified vitamin $D_3$ derivatives.

The basic concept of this synthesis is the elaboration of the desired vitamin D compound by coupling the appropriate and separately synthesized side chain unit to a preformed vitamin D nucleus bearing a displaceable group at carbon-22. The required side chain unit is prepared as a phenylsulfone derivative, and the required vitamin D nucleus, when 1α-hydroxyvitamin D-type compounds are the synthetic objective, is a secosterol derivative of the following structure:

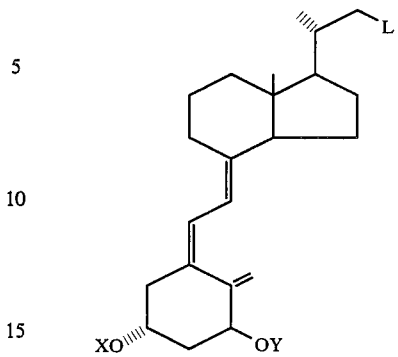

wherein X and Y represent hydrogen or hydroxy-protecting groups, and where L is a leaving group such as halide, or a tosyloxy or mesyloxy or similar displaceable function. A preferred derivative of this type is the hydroxy-protected vitamin D-22-tosyloxy compound. The necessary phenylsulfone compounds used for the construction of the desired side chain have the following structure:

$$PhSO_2-CH_2-R$$

where Ph represents a phenyl or alkyl substituted phenyl group, and where R is selected from the group consisting of alkyl, and hydroxy- and fluoro-substituted alkyl, where the hydroxy groups are preferably derivatized by hydroxy-protecting groups.

The coupling between the above described vitamin D-22-tosylate, and the appropriate phenylsulfone unit, is based on established principles of sulfone chemistry [e.g. see P. D. Magnus, Tetrahedron 33, 2019 (1977); Trost et al., Tetrahedron Letters, 3477 (1976)]. The reaction, mediated by a strong base, yields an adduct, which may be represented by the following structure:

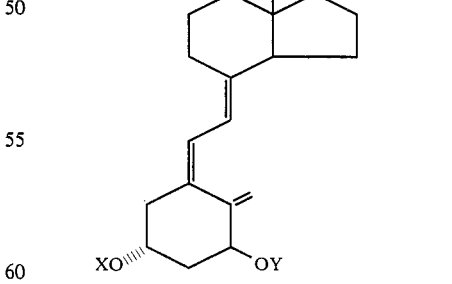

wherein R, X and Y represent groupings as defined above. Intermediary adducts of the type shown above, which are new compounds, may then be reduced in a medium containing a metal amalgam (e.g. sodium amalgam, aluminum amalgam) to produce the desired vitamin D compound of the general structure:

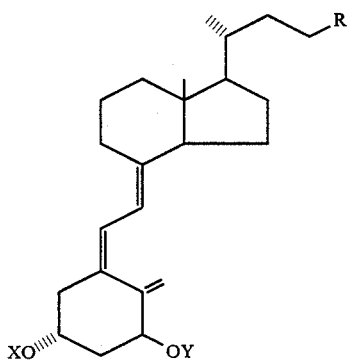

Reductive desulfonation can also be achieved by other means, such as dissolving metal reductions, using, for example, metal/alkylamine or metal/NH$_3$ mixtures. Hydroxy-protecting groups can then be removed by standard methods known in the art, so as to produce the corresponding free hydroxy compounds.

The above described vitamin D-22-tosylate starting material for the side chain coupling process of this invention is a known substance which can be prepared by known methods [e.g. Andrews et al., J. Org. Chem. 51, 4819 (1986)]. It can also be prepared by hydride reduction, and subsequent tosylation of a vitamin D-22-ester [see also Kutner et al., Tet. Letters 28, 6129–6132 (1987)] having the following structure:

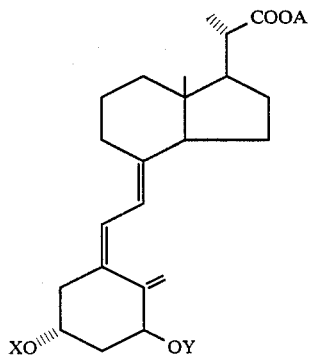

wherein X and Y are hydrogen or hydroxy-protecting groups, and where A represents an alkyl or aryl group. The preparation and use of these novel esters as part of the present synthesis of vitamin D compounds is another aspect of this invention.

It is evident that the above-described process, using the vitamin D-22-tosylate as the vitamin nucleus and a suitable phenylsulfone as the side chain residue, can be used for the preparation of many 1α-hydroxyvitamin D side chain analogs, depending upon the alkyl or hydroxy-alkyl radical R selected. Preferred phenylalkyl sulfone units, are those compounds in which R is an alkyl or a hydroxy-alkyl radical of the following general structures:

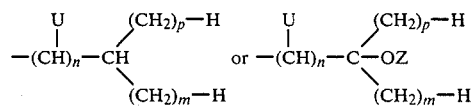

where U is selected from the group consisting of hydrogen, hydroxy, protected-hydroxy, or a hydrocarbon radical of 1 to 4 carbons, and where l, m, and n are integers having, independently, the values 1 to 5, and where Z is hydrogen or a hydroxy-protecting group. Especially preferred for the preparation of novel compounds having the desired biological activity (i.e. high differentiation activity and no or low calcemic activity) are the sulfone units shown above in which n has the values 3 or 4.

As used in the description and in the claims, the term hydroxy-protecting group signifies any group commonly used for the temporary protection of hydroxy functions, such as for example, acyl, alkylsilyl, and alkoxyalkyl groups, and a protected hydroxy group is a hydroxy function derivatized by such a protecting group. The term 'acyl' signifies an alkanoyl group of 1 to 6 carbons, in all of its isomeric forms, or a carboxyalkanoyl group of 1 to 6 carbons, such as an oxalyl, malonyl, succinyl, glutaryl group, or a aromatic acyl group such as benzoyl, or a halo, nitro or alkyl substituted benzoyl group. The word 'alkyl' as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred alkylsilyl-protecting groups are trimethylsilyl, triethylsilyl, t-butyldimethylsilyl, and analogous alkylated silyl radicals.

The present invention is more specifically described by the following examples, which are meant to be illustrative only of the process of synthesis and of the novel compounds obtainable thereby. In these examples, specific compounds identified by Arabic numerals (e.g. compounds 1, 2, 3, . . . etc.) refer to the structures so numbered in the process schematics. Additionally, examples are provided illustrative of the distinctive biological characteristics of the new compounds, such characteristics serving as basis for the application of these compounds as cell differentiation and antineoplastic agents.

Preparation of Compounds General Procedures

Infrared spectra (IR) were obtained on a Nicolet MX-1 FT-IR spectrometer using neat films of oily substances. Ultraviolet (UV) absorption spectra were recorded with a Hitachi Model 60-100 UV-VIS spectrometer. Nuclear magnetic resonance (NMR) spectra were recorded at 270 or 400 MHz with Bruker WH-270 or AM-400 FT spectrometers in the solvents noted. Chemical shifts (δ) are reported downfield from internal Me$_4$Si (δ0.00) or CHCl$_3$ (δ7.24). Low- and high-resolution mass spectra were recorded at 70 eV (unless otherwise stated) on a Kratos MS-50 TC instrument equipped with a Kratos DS-55 Data System. High resolution data were obtained by peak matching. Samples were introduced into the ion source maintained at 120°–250° C. via a direct-insertion probe. Silica gel 60 (Merck, 70–230 or 230–400 mesh) was used for column chromatography. Thin-layer chromatography (TLC) was performed using precoated aluminum silica gel sheets with UV indicator from EM Science (Gibbstown, NJ). Solvent systems used: A: chloroform-ethanol 85:15 (v/v); B: hexane-ethyl acetate 1:1, and C: hexane-ethyl acetate 3:1. High performance liquid chromatography (HPLC) was performed using a Waters Associates Liquid chromatograph equipped with a model 6000A solvent delivery system, a Model 6 UK Universal injector and a model 450 variable wavelength detector. Zorbax-Silica (Phenomenex) columns (6.2 mm+25 cm and 10 mm×25 cm) were used. Solvent systems: A: 3% 2-propanol in hexane; B: 2% 2-propanol in hexane; C: 6% 2-propanol in hexane; D: 10% 2-propanol in hexane; E: 20% 2-propanol in hexane; F: 2% ethyl acetate in hexane. Silica gel Sep-Pak (Waters Associates) cartridges were used for the prefiltration of HPLC samples. 3β-Acetoxy-22,23-bisnor-5-cholenic acid was purchased from Steraloids (Wilton, NH). Tetrahydrofuran (THF) was distilled from sodium benzophenone ketyl. Other solvents were purified by standard methods. n-Butyllithium in hexane (Aldrich) was titrated with n-propanol in the presence of 1,10-phenantroline in THF under argon. Reactions involving vitamin D compounds were carried out under a nitrogen or argon atmosphere with magnetic stirring. Solutions and liquids were delivered by syringes through rubber septa.

EXAMPLE 1

Synthesis of 1α-hydroxyvitamin C-22 ester (compound 10) and hydroxy-protected derivatives (compounds 8, 11) (Process Scheme I)

(a) Preparation of steroid esters 1 and 2

3β-Acetoxy-22,23-bisnor-5-cholenic acid (10 g) was dissolved in 420 ml of 5% KOH in methanol and the solution was stirred at ambient temperature for 15 min to hydrolyze the acetate. To this solution, 160 mL of 10% $H_2SO_4$ in methanol was added dropwise with stirring and the resulting suspension was diluted with 400 mL of 1% $H_2SO_4$ in methanol. The mixture was heated under reflux for 48 h to complete the esterification (checked by TLC, solvent system A). The product, the methyl ester (1) (9.0 g, 88%) was isolated by standard procedure, and 4.4 g (12 mmol) of that material was dissolved in 135 mL of dry dimethylformamide (DMF) and imidazole (3.6 g, 52.8 mmol) was added, followed by tert-butyldimethylsilyl chloride (4.0 g, 26.4 mmol). The solution was stirred at room temperature for 5 min until the bulky precipitate was formed and then stirring was continued for an additional 15 min. The reaction mixture was extracted with hexane (400 mL), washed with water, saturated NaCl solution, and dried over $MgSO_4$. Evaporation of the solvent provided TLC pure (solvent system b) silylated ester 2 (5.3 g) as a colorless oil that was used for the next step without further purification. An analytical sample was obtained by flash chromatography using 2% ethyl acetate in hexane: IR (firm) 1737.99, 1604.89 $cm^{-1}$.

(b) Preparation of 5,7-diene (3)

A mixture of compound (2) (1.0 g, 2.1 mmol), dibromantin (0.42 g, 1.5 mmol) and anhydrous sodium bicarbonate (0.91 g, 10 mmol) in 20 mL of hexane was heated under reflux in a nitrogen atmosphere for 30 min until no starting ester 2 was detected (TLC, system C). The precipitate was filtered and the solution dried down under reduced pressure. The residue was redissolved in 5 mL of anhydrous THF, tetrabutylammonium bromide (0.06 g, 0.19 mmol) was added and the mixture stirred at room temperature for 30 min under nitrogen. A solution of tetrabutylammonium fluoride (10 mL, 1M in THF) was then added followed by 0.7 mL of s-collidine and the mixture was stirred under nitrogen at room temperature for 1 h. Another 5 mL of tetrabutylammonium fluoride solution was added and stirring was continued for 3 h. Ether (50 mL) was added and the organic phase was washed with water, cold 1N HCl, 10% $NaHCO_3$ and dried over anhydrous $MgSO_4$. The product, dissolved in benzene was chromatographed on silica gel 70-230 mesh (30 g). Ester 3 (0.44 g, 58%) was eluted using ethyl acetate in hexane. An analytical sample was obtained by HPLC, solvent system A, $R_v$ 77 mL: UV (3% 2-propanol in hexane), $\lambda_{max}=262$ nm ($\epsilon 7{,}000$), $\lambda_{max}=272$ nm ($\epsilon 9{,}800$), $\lambda_{max}=282$ nm ($\epsilon 10{,}500$), $\lambda_{max}=293$ ($\epsilon 6{,}000$); $^1$H NMR ($CDCl_3$) δ, 0.54 (s, 3H, 18-$CH_3$), 0.94 (s, 3H, 19-$CH_3$), 1.22 (d, 2H, J=6 Hz, 21-$CH_3$), 3.6 (m, 1H, 3-H), 3.68 (s, 3H, $CO_2CH_3$), 5.42 (m, 1H, 6-H), 5.58 (m, 1H, 7-H); MS, m/z (relative intensity) M+ 358 (61), 340 (12), 325 (100), 299 (68), 271 (7), 253 (17), 237 (26), 211 (27), 143 (72), 119 (35).

(c) Preparation of vitamin ester (4)

A solution of diene 3 (830 mg, 2.3 mmol) in 350 mL of benzene-ethyl ether, 1:4 (v/v) was irradiated with stirring under nitrogen in a water-cooled quartz immersion well equipped with a nitrogen bubbler and a Vycor filter using Hanovia 608A36 medium-pressure UV lamp for 40 min (4×10 min). The reaction was monitored by HPLC using 2% 2-propanol in hexane at 265 nm. Solution was dried down under reduced pressure, redissolved in 100 mL of absolute ethanol and heated under reflux in a nitrogen atmosphere for 3 h. Then the solution was concentrated, redissolved in 1 mL of 10% ethyl acetate in hexane and chromatographed on silica gel 70-230 mesh (30 g). Vitamin ester 4 (298 mg, 36%) was eluted using a mixture of 15% ethyl acetate in hexane. An analytical sample was obtained by HPLC, solvent system B, $R_v$ 94 mL: IR (film) 1738.95 $cm^{-1}$; UV, $\lambda_{max}$ 264 nm; $^1$H NMR ($CDCl_3$), δ, 0.56 (3H, s, 18-$CH_3$), 1.20 (3H, d, J=7 Hz, 21-$CH_3$), 3.66 (3H, s, $CO_2CH_3$), 3.95 (1H, m, 3-H), 4.80 (1H, d, J=1.2 Hz, 19Z-H), 5.05 (1H, d, J=1.2 Hz, 19E-H), 6.03 (1H, d, J=11 Hz, 7-H), 6.23 (1H, d, J=11 Hz, 6-H); MS, m/z (relative intensity), M+ 358 (45), 340 (9), 325 (45), 299 (22), 253 (19), 237 (18), 136 (60), 118 (100).

(d) Preparation of 3,5-cyclovitamin ester (6)

Ester 4 was converted into tosylate 5 by the known method using p-toluenesulfonyl chloride in pyridine at 4° C. for 20 h. Crude tosylate 5 (102 mg, 0.2 mmol), dissolved in 2 mL of anhydrous dichloromethane, was added with stirring to a methanol solution (15 mL) containing anhydrous potassium bicarbonate (250 mg), at 55° C. The mixture was stirred under nitrogen at 55° C. for 24 h. The solvents were then removed under reduced pressure and the residue extracted with ether. The organic phase was washed with water and dried over anhydrous $MgSO_4$. The product, cyclovitamin ester 6, was purified by silica gel chromatography using 20% ethyl acetate in hexane (50 mg, 68%): $^1$H NMR ($CDCl_3$), δ0.54 (3H, s, 18-$CH_3$), 0.74 (m, 3H), 0.91 (m, 4-H), 1.20 (3H, d, J=7 Hz, 21-$CH_3$), 3.25 (3H, s, 6R-$OCH_3$), 3.65 (3H, s, 22-$CO_2CH_3$), 4.15 (1H, d, J=9 Hz, 6-H), 4.88 (1H, 19E-H), 5.00 (1H, d, J=9 Hz, 7-H), 5.02 (1H, 19E-H), MS, m/z (relative intensity) 372 (M+, 17), 340 (100), 253 (48), 221 (40), 135 (72).

(e) Preparation of 5,6-cis 1α-hydroxyvitamin ester (8) and trans isomer (9).

Tert-butyl hydroperoxide (112 μL, 3.0M solution in toluene, 0.34 mmol) was added to a suspension of selenium dioxide (9 mg, 0.8 mmol) in 2 mL of dry methylene chloride. The mixture was stirred at room temperature under nitrogen until a clear solution was formed. Anhydrous pyridine (12 μL, 0.15 mmol) was then added followed by ester 6 (50 mg) dissolved in 2 mL of anhydrous dichloromethane. The mixture was stirred under nitrogen for 30 min. Cold 10% sodium bicarbonate (2 mL) was added and the mixture extracted with ether. The organic phase was washed with cold 10% sodium bicarbonate ice water and dried over anh. MgSO$_4$. Silica gel chromatography (10–20% ethyl acetate in hexane) afforded 12.5 mg of the 1α-hydroxy compound (7). This product was then immediately dissolved in 0.5 mL of glacial acetic acid and the solution was heated at 55° C. with stirring under nitrogen for 15 min. The reaction mixture was poured over ice, extracted with ether and washed with ice-cold saturated sodium bicarbonate. The combined ether extracts were washed with water and dried over anh. MgSO$_4$. Ester 8 was isolated (6 mg, 20% overall yield from 5) by the general procedure described by DeLuca et al., U.S. Pat. No. 4,554,106. Analytical samples of (5Z,7E) and 5E,7E) isomers, 8 and 9, respectively, were obtained by preparative HPLC in a ratio of 2.5:1.

Compound (8): HPLC, solvent system C, R$_v$ 68 mL; UV (EtOH) $\lambda_{max}$ 264 nm, $\lambda_{min}$ 227 nm, $$\frac{A264}{A227} = 2.07;$$

$^1$H NMR (CDCl$_3$) δ, 0.56 (3H, s, 18-CH$_3$), 1.20 (3H, d, J=6.5 Hz, 21-CH$_3$), 2.04 (3H, s, 3β-acetyl), 3.66 (3H, s, 22-CO$_2$CH$_3$), 4.4 (1H, m, 1-H), 5.2 (1H, m, 3-H), 5.01 (19E-H), 5.34 (19Z-H), 6.01 (1H, d, J=10 Hz, 7-H), 6.33 (1H, d, J=10 Hz, 6-H), MS, m/z (relative intensity), 416 (M$^+$, 4), 356 (100), 338 (21), 251 (13), 134 (95).

Compound (9): HPLC, solvent system C, R$_v$ 78 ml; UV (EtOH), $\lambda_{max}$ 267 nm, $\lambda_{min}$ 227 nm, $$\frac{A267}{A227} = 3.51;$$

$^1$H NMR (CDCl$_3$) δ, 0.56 (3H, s, 18-CH$_3$), 1.20 (3H, d, J=6.5 Hz, 21-CH$_3$), 2.04 (3H, s, 3β-OAc), 3.66 (3H, s, 22-CO$_2$CH$_3$), 4.5 (1H, m, 1-H), 5.3 (1H, m, 3-H), 4.99 (19E-H), 5.13 (19Z-H), 5.81 (1H, d, J=10 Hz, 7-H), 6.56 (1H, d, J=10 Hz, 6-H).

(f) Preparation of 1α-hydroxy ester (10) and disilyl ester (11)

A 0.1N solution of KOH in methanol (10 mL) was added to a stirred solution of acetate ester 8 (100 mg, 0.24 mmol) in ethyl ether (10 mL). The resulting solution was stirred at room temperature for 90 min until no starting material was detected by TLC (solvent system B). Dihydroxyester (10) was isolated by standard extraction procedure (ethyl acetate, saturated NaCl, anhydrous MgSO$_4$).

A mixture of imidazole (250 mg, 3.6 mmol) and tert-butylimethylsilyl chloride (250 mg, 1.6 mmol) in DMF (2 mL) was added to a stirred solution of ester (10) (86.2 mg, 0.23 mmol) in 4 mL of DMF. The resulting homogenous mixture was stirred for 15 min at 55° C. until no starting material was detected by TLC (solvent system B). The product was isolated with hexane and the organic extract was washed with brine and dried over anhydrous MgSO$_4$. A hexane solution of the crude product was filtered through silica gel Sep-Pak cartridge to give the disilylated ester (11) (136 mg, 98%): UV (hexane), $\lambda_{max}$ 264 nm, $\lambda_{min}$ 227 nm, $$\frac{A264}{A227} = 1.91;$$

$^1$H NMR (CDCl$_3$), δ0.07 [12H, s, Si(CH$_3$)$_2$], 0.55 (3H, s, 18-CH$_3$), 0.86 [18H, s, C(CH$_3$)$_3$], 1.20 (3H, d, J=6.8 Hz, 21-CH$_3$), 3.65 (3H, s, O—CH$_3$), 4.18 (1H, m, 3-H), 4.36 (1H, m, 1-H), 4.83 (1H, d, J=1.2 Hz, 19Z-H), 5.16 (1H, d, J=1.2 Hz, 19E-H) 5.96 (1H, d, J=11.2 Hz, 7-H), 6.19 (1H, d, J=11.2 Hz, 6-H); MS, m/z (intensities normalized to m/e 248), 602 (M$^+$, 10), 470 (59), 413 (7), 338 (10), 248 (100).

EXAMPLE 2

Synthesis of C-22-alcohol (12) and C-22-tosyl derivative (13) (Process Scheme II)

(a) Preparation of C-22-alcohol (12)

Lithium aluminum hydride (25 mg, 0.65 mmol) was added to stirred solution of silyl ester (11) (136.2 mg, 0.23 mmol) in anhydrous THF (5 mL) under argon at 0° C. The suspension was stirred for 15 min at 0° C. and the excess of LiAlH$_4$ was decomposed by the dropwise addition of 10% H$_2$O in THF. The suspension was diluted with 10 mL of THF and the stirring was continued for an additional 15 min at room temperature. The product was isolated by the standard extraction with ethyl acetate and silica gel Sep-Pak filtration in 10% ethyl acetate in hexane. Disilyl alcohol 12 was obtained as a colorless oil (118.4 mg) in 91% yield: UV (EtOH), $\lambda_{max}$ 264, $\lambda_{min}$ 227, $$\frac{A264}{A227} = 1.57;$$

$^1$H NMR (CDCl$_3$) δ0.00 (12H, s, Si—CH$_3$) 0.53 (3H, s, 18-CH$_3$), 0.85 [18H, s, Si—C(CH$_3$)$_3$], 1.04 (3H, d, J=6.4 Hz, 21-CH$_3$), 3.37 and 3.63 (1H and 1H, each m, 22-CH$_2$), 4.17 (1H, m, 3-H), 4.35 (1H, m, 1-H), 4.84 (1H, brs, 19Z-H), 5.16 (1H, brs, 19E-H), 6.0 (1H, d, J=12.2 Hz, 7-H), 6.21 (1H, d, J=12.2 Hz, 6-H); MS, m/z (intensities normalized to m/e 248), 574 (M$^+$, 17), 442 (67), 383 (11), 308 (17), 248 (100).

(b) Preparation of 22-alcohol-tosylate (13)

An ice-cold solution of p-toluenesulfonyl chloride (42.7 mg, 0.22 mmol) in dry pyridine (50 μL) was added to a stirred solution of alcohol 12 at 0° C. under nitrogen. The mixture was stirred at 5° C. for 22 h until no starting material was detected by TLC using the solvent system C. The reaction mixture was poured over ice-cold saturated aqueous NaHCO$_3$ and stirring was continued for another 30 min. The product was extracted with ethyl ether-hexane 1:1 (v/v). The organic phase was washed with saturated NaCl and dried over MgSO$_3$. Solvents were removed under reduced pressure and pyridine was removed in a stream of nitrogen. Crude product was purified by silica gel Sep-Pak filtration (5% ethyl acetate in hexane) to give pure tosylate 13 (54 mg, 98%): IR (film) 3500, 2950, 1580, 1367, 1267, 1189, 1178, 1099, 1085, 835 cm$^{-1}$; UV (hexane) $\lambda_{max}$ 263 nm, $\lambda_{min}$ 236 nm; $^1$H NMR (CDCl$_3$) δ0.00 (12H, s, Si—CH$_3$), 0.43 (3H, s, 18-CH$_3$), 0.81 [18H, s, Si-C(CH$_3$)$_3$], 0.93 (3H, d, J=6.8 Hz, 21-CH$_3$), 2.40 (3H, s, Ar—CH$_3$), 3.64 and 3.91 (1H and 1H, each m, 22-CH$_2$), 4.13 (1H, m, 3-H), 4.31 (1H, m, 1-H), 4.79 (1H, brs, 19Z-H), 5.13 (1H, brs, 19E-H), 5.94 (1H, d, J=12.8 Hz, 7-H), 6.17 (1H, d, J=12.8 Hz, 6-H), 7.43 and 7.84 (2H and 2H, each m, Ar-H); MS m/z (intensity relative to m/z 248), 728 (6), 596 (30), 556 (7), 464 (7), 424 (44), 367 (19), 292 (23), 248 (100); exact mass calcd. for $C_{41}H_{68}O_5Si_2S$ 728.4338, found 728.4326.

EXAMPLE 3

Synthesis of phenylsulfone side chain units (Process Scheme III)

(a) Preparation of phenylsulfone side chain residue 18

A solution of 4-chlorovaleryl chloride 14 (Aldrich; 3 g, 19.2 mmol) in anhydrous THF (25 mL) was added dropwise with vigorous stirring, over 30 min, under argon, to a solution of methylmagnesium bromide (12.9 mL of a 3M solution in ether) in 25 mL of dry THF at $-10°$ C. The reaction mixture was then allowed to warm up to room temperature within 2 h, then quenched with water and neutralized with diluted hydrochloric acid. The mixture was extracted with ether, the combined organic layers were washed with water and dried with sodium sulfate. After removal of the solvent, the residue was distilled in vacuo to give chloroalcohol 15 as a colorless liquid (2.1 g, 70%). Product 15 (1.5 g, 10 mmol) in anhydrous dimethylformamide (5mL) was then added to a stirred solution of thiophenol (1.32 g, 12 mmol) and potassium t-butoxide (1.32 g, 11.3 mmol) in anhydrous dimethylformamide (25 mL). The reaction mixture was stirred at room temperature overnight and the solution was partitioned between dichloromethane and water. The organic layer was washed with aqueous sodium carbonte, water and dried over anhydrous magnesium sulfate. The solvent was evaporated in vacuo and the crude oil was purified by silica gel flash chromatography with hexane-ethyl acetate. Sulfide 16 (2.2 g, 98%) was obtained as a colorless liquid. Sulfide 16 (1.01 g, 4.5 mmol) was then dissolved in dry dichloromethane (40 mL) and 3-chloroperbenzoic acid (2.5 g, 11.6 mmol; Aldrich 80-85%) was added in portions with stirring and occasional cooling. The reaction mixture was stirred for 2 h and then quenched with 10% sodium bicarbonate. The combined organic extracts were washed with aqueous sodium sulfite and brine and dired over magnesium sulfate. The solvent was removed in vacuo and the crude oil was purified by silica gel flash chromatography using hexane-ethyl acetate mixtures to afford sulfone 17 (1.1 g, 97%) as a colorless liquid. To a stirred solution of sulfone 17 (1.3 g, 5.1 mmol) and imidazole (1.5 g, 22.7 mmol) in dry dimethylformamide (50 mL), triethylsilyl chloride (1.15 g, 7.7 mmol) was added. The reaction mixture was kept at room temperature for 2 h and then diluted with dichloromethane. The mixture was washed with aqueous ammonium chloride solution and water. The organic layers were dried over sodium sulfate and the solvent removed in vacuo. The residue was purified by silica gel flash chromatography. Hexaethyldisiloxane was first eluted with hexane. The triethylsilyl-protected sulfone 18 (1.8 g, 97%) was eluted with hexane-ethyl acetate 9:1 as a colorless liquid: IR (neat): 3045, 2940, 1440, 1360, 1130, 1020 $cm^{-1}$; $^1H$ NMR (400 MHz, $CDCl_3$) $\delta$0.518 (6H, q, J=6.2 Hz, Si—$CH_2$), 0.899 (9H, t, J=6.2 Hz, Si—C—$CH_3$), 1.142 (6H, s, $CH_3$), 1.307-1.462 (4H, m), 1.655-1.738 (2H, m, H-4), 3.080-3.122 (2H, m, H-2), 7.567 (2H, t, J=6.8 Hz, H-aryl meta), 7.648 (1H, t, J=6.8 Hz, H-aryl para), 7.916 (2H, d, J=6.83 Hz, H-aryl ortho); MS (EI, 7 eV): m/z (relative intensity) 372 ($M^+$, 2), 341 (100), 229 (2), 227 (18), 173 (24), 103 (22), 75 (45), 55 (33).

As shown by the illustrative examples of Process Scheme III, other phenylsulfone units can be prepared by the general method described above, or by analagous methods described in the literature. For example:

(b) Preparation of phenylsulfone (19)

By treatment of dichloro compound 14 according to the procedure described in Example 3(a) above, but substituting ethylmagnesium bromide for methylmagnesium bromide in the first reaction step, there is obtained the phenylsulfone homolog of structure 19 (Z=$Et_3Si$).

(c) Preparation of phenylsulfone (23)

A solution of 6-bromohexanoyl chloride (20, 3.8 g, 2.8 mL, 18 mmol) in anhydrous tetrahydrofuran (10 mL) was added dropwise with vigorous stirring over 15-20 min under argon atmosphere to a solution of methylmagnesium bromide (14 mL of 3M solution in ether) in anhydrous tetrahydrofuran (15 mL) at $-10°$ C. The mixture was stirred at room temperature for 2 h, cooled to 0° C. and carefully decomposed with 1:1 diluted hydrochloric acid. The mixture was extracted with ether, the combined organic layers were washed with water, dried over anhydrous magnesium sulfate and evaporated to give the bromo alcohol (21) as a colorless oil (3.6 g, 94%).

The bromo-alcohol (3.4 g, 16 mmol) was treated with benzene sulfinic acid sodium salt (3.3 g, 20 mmol) in anhydrous dimethylformamide at 70° C. for $4\frac{1}{2}$ h. The mixture was poured on ice, extracted with dichloromethane, washed with 1N HCl, water, 10% $NaHCO_3$ solution, dried over anhydrous $MgSO_4$, filtered and evaporated to give the sulfone (22), which was purified by flash chromatography on silica gel and eluted with 40-50% ethyl acetate in hexane to give the sulfone containing some of the corresponding sulfinate ester (4.18 g, 98%), MS, m/z (270 ($M^+$), 255 ($M^+$-15), 77, 59.

To a stirred solution of the sulfone (22) (4 g, 14 mmol) and imidazole (3.8 g, 55 mmol) in anhydrous dmethylformamide (13 mL) triethylsilyl chloride (4.6 g, 5.1 mL, 30 mmol) was added. The reaction mixture was stirred at room temperature for 2 h, poured on ice water, extracted with ether, dried over anhydrous $MgSO_4$, filtered and evaporated. The residue was purified by flash chromatography. Hexaethyldisiloxane was first eluted with hexane; 3% ethyl acetate in hexane eluted the protected sulfinate ester with some of the sulfone, and 10% ethyl acetate in hexane eluted the protected pure sulfone (23) (3.4 g, 60%). Anal. calcd. for $C_{20}H_{36}O_3SSi$ C, 62.45%, H, 9.43%, S 38.34%, Found C, 61.97%, H, 9.45%, S, 8.33%. MS, m/z (relative intensity) 355 (100) ($M^+$-29), 227 (15), 173 (35), 103 (43), 75 (95), 55 (23), NMR (400 MHz, $CDCl_3$), 0.54 (6H, q, J=7 Hz, Si—$CH_2$), 0.94 (9H, t, J=8 Hz, Si—C—$CH_3$), 1.15 (6H, s, $CH_3$), 1.31-1.36 (4H, m), 3.08-3.12 (2H, m, H-2), 7.57 (2H, t, J=6.8 Hz, H-aryl-meta), 7.66 (1H, t), H-aryl para), 7.92 (2H, d, J=6.8 Hz, H-aryl ortho).

(d) Preparation of phenylsulfone (26)

Treatment of the commercially available 3-phenylsulfonylpropionic acid (24) with acidic methanol under standard esterification conditions provides the corresponding methyl ester, which is then subjected to a Grignard reaction using methyl magnesium bromide to obtain the phenylsulfone derivative (25). The reaction of (25) with triethylsilylchloride, using the conditions of Example 3(a) above, then gives the hydroxy-protected sulfone (26).

(e) Preparation of sulfone unit (28)

By application of the procedure given in Example 3(d) to acid (24), but substituting ethylmagnesium bromide for methylmagesium bromide in the Grignard reaction step, there is obtained the protected-sulfone homolog (28).

As illustrated by the above examples, the phenylsulfone units are preferably prepared, and subsequently used, as hydroxy-protected derivatives. In addition to triethylsilyl-protecting group, other preferred hydroxy-protecting groups are t-butyldimethylsilyl, tetrahydrofuranyl, and tetrahydropyranyl.

EXAMPLE 4

Side chain coupling reaction (Process Scheme IV)

(a) Preparation of vitamin sulfones 29 and 30

A solution of 1,10-phenanthroline (used as indicator) in anhydrous THF was added under argon to the 1.35M solution of n-BuLi in hexane (48 μL, 64 μmol) to obtain a dark-red color of the mixture. The solution was placed in an acetone-dry ice bath and diisopropylamine (9 μL, 64 μmol) was added. The resulting solution was stirred under argon for 30 min at −77° C. Then the solution of sulfone 18 (29 mg, 80 μmol) in 100 μL of THF was added followed by another 100 μL of THF used in rinsing. The resulting brown mixture was stirred at −75° C. under argon for 30 min and the cooling bath was replaced with CCl4 dry ice bath. After 15 min of stirring at −21° C. the solution of tosylate 13 (11.6 mg, 16 μmol) was added and the color of the reaction mixture turned black to red. The solution was stirred at −20° to −10° C. for 3.5 h and 1 mL of saturated NH4Cl was added at −10° C. The mixture was extracted with hexane and the organic phase was washed with saturated NaCl.

The organic extract was filtered through silica gel Sep-Pak cartridge followed by 20 mL of 10% ethyl acetate in hexane. Preparative HPLC (column 6.2×25 cm) with solvent system F provided at R$_v$ 37 mL the unreacted tosylate 13 (3.0 mg). Sulfone 29 (2.1 mg, 19%) was then eluted at R$_v$ 55 mL: IR (film) 3500, 2956, 1440, 1301, 1258, 1147, 1086, 1072, 1064 cm$^{-1}$; UV (hexane) λ$_{max}$ 264 nm, λ$_{min}$ 230 nm, $$\frac{A264}{A230} = 1.96;$$

$^1$H NMR (CDCl$_3$) δ0.41 (3H, s, 18-CH$_3$), 0.51 (6H, q, J=5.7 Hz, Si—CH$_2$—), 0.86 and 0.88 [9H and 9H, each, s, Si—C(CH$_3$)$_3$], 0.90 (9H, t, J=8 Hz, SiCH$_2$—CH$_3$), 1.13 (3H, d, J=5.8 Hz, 21-CH$_3$), 1.23 (6H, s, 26,27-CH$_3$), 4.17 (1H, m, 3-H, 4.37 (1H, m, 1-H), 4.85 (1H, brs, 19Z-H), 5.17 (1H, brs, 19E-H), 5.99 (1H, d, J=11.0 Hz, 7-H), 6.21 (1H, d, J=10.8 Hz, 6-H), 7.54 (2H, t, J=7.3 Hz, Ar-H, meta), 7.61 (1H, t, J=7.3 Hz, Ar-H para), 7.33 (2H, d, J=7.3 Hz, Ar-H, ortho); MS, m/z (relative intensity), 926 (M+, 16), 794 (100), 737 (9), 530 (9), 521 (6), 389 (13), 301 (8).

Sulfone 30 (3.8 mg, 35%) (epimer of 29 at carbon 23) was eluted at R$_v$ 87 mL: IR (film) 3500, 2955, 1440, 1304, 1257, 1148, 1086, 1072, 1064 cm$^{-1}$; UV (hexane) λ$_{max}$ 264 nm, λ$_{min}$ 229 nm, $$\frac{A264}{A229} = 2.06;$$

$^1$H NMR (CDCl$_3$) δ0.49 (3H, s, 18-CH$_3$), 0.51 (6H, q, J=5.7 Hz, Si—CH$_2$—), 0.85 [18H, s, Si—C(CH$_3$)$_3$], 0.90 (9H, t, J=7.9 Hz, Si—CH$_2$—CH$_3$), 1.13 (3H, d, J=6.2 Hz, 21-CH$_3$), 1.23 (6H, s, 26,27-CH$_3$), 4.16 (1H, m, 3-H), 4.35 (1H, m, 1-H), 4.83 (1H, brs, 19Z-H), 5.16 (1H, brs, 19E-H), 5.98 (1H, d, J=Hz, 7-H), 6.20 (1H, d, J=11.3 Hz, 6-H), 7.54 (2H, t, J=7 Hz, Ar-meta), 7.61 (1H, t, J=7 Hz, Ar-H, para), 7.86 (2H, d, J=7 Hz, Ar-H ortho); MS m/z (relative intensity), 926 (19), 794 (100), 737 (11), 530 (28), 521 (14), 389 (33), 301 (14).

(b) 24-dihomo-1,25-dihydroxyvitamin D$_3$ (32)

A saturated solution of Na$_2$HPO$_4$ in methanol (0.5 mL) was added to a stirred solution of sulfone 29 (1.80 mg) in 0.5 mL of anhydrous THF followed by powdered anhydrous Na$_2$HPO$_4$ (80 mg). The mixture was stirred under argon for 30 min and cooled down to 0° C. Fresh 5% sodium amalgam (ca. 200 mg) was then added and the mixture was stirred for 3 h at 5° C. until no starting material was detected by TLC (solvent system C). The mixture was diluted with hexane (3 mL) and stirring was continued for 15 min. Solvents were decanted and the solid materials were washed with hexane (3×2 mL). Ice and saturated NaCl (2 mL) was added to the combined organic solutions. The organic layer was washed with saturated NaCl and filtered through silica Sep-Pak cartridge to give the hydroxy-protected 24-dihomo-1α,25-dihydroxyvitamin D$_3$ compound 31 (1.19 mg, 1.5 μmol, 78%) as a colorless oil. Compound 31 was also obtained the same way by the sodium amalgam reduction of sulfone 30. Thus, sulfones 29 and 30, as obtained in Example 4(a) above, need not be separated prior to the sodium amalgam reduction. A mixture of both can be effectively reduced to obtain the desired vitamin D derivative 31.

Compound 31 (1.1 mg) was dissolved in 0.5 mL of anhydrous THF and to this solution tetrabutylammonium fluoride in THF (20 μL, 1M solution) was added. The mixture was stirred under argon for 50 min at 50° C. Ether (3 mL) was then added and the organic phase was washed with saturated NaCl. Solvents were removed and the residue was dissolved in 10% 2-propanol in hexane and filtered through silica Sep-Pak. Preparative HPLC (solvent system D, column 6.2 mm×25 cm, R$_v$ 62 mL) yielded the desired vitamin D homolog 32 (465 μg, 76%); IR (film) 3360, 2927, 1602, 1447, 1376, 1297, 1146, 1106, 1086, 1064 cm$^{-1}$; UV (10% 2-propanol in hexane) λ$_{max}$ 264 nm, λ$_{min}$ 228 nm, $$\frac{A264}{A228} = 1.91;$$

$^1$H NMR (CDCl$_3$) δ 0.52 (3H, s, 18-CH$_3$), 0.90 (3H, d, J=6.4 Hz, 21-CH$_3$), 1.19 (6H, s, 26, 27-CH$_3$), 4.22 (1H, m, 3-H), 4.42 (1H, m, 1-H), 4.99 (1H, brs, 19Z-H), 5.31 (1H, brs, 19E-H), 6.00 (1H, d, J=11.1 Hz, 7-H), 6.36 (1H, d, J=11.2 Hz, 6-H); MS m/z (relative intensity) 444 (M+, 1.4), 426 (41), 393 (10), 251 (26), 209 (17), 197 (20), 157 (29), 155 (37), 134 (58), 105 (54), 59 (100); exact mass calcd. for C$_{29}$H$_{48}$O$_3$ 444.3603, found 444.3609.

(c) Side Chain Coupling using phenyl sulfone (23)

Vitamin tosylate 13 is reacted with the phenylsulfone units 23 under the conditions described in Example 4(a) above, to obtain the corresponding vitamin sulfone adduct. After Na/Hg reduction of that adduct, using the general conditions of Example 4(b) above, and subsequent removal of the hydroxy-protecting groups as described in Example 4(b), there is obtained the desired product, 24-trihomo-1,25-dihydroxyvitamin $D_3$, characterized by the structure below:

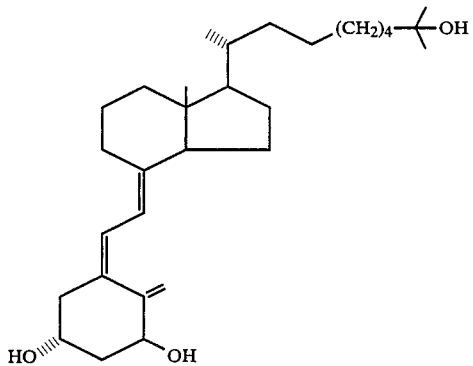

Biological Activity of
24-dihomo-1,25-dihydroxyvitamin $D_3$ (Compound 32)

EXAMPLE 5

Measurement of Differentiation in HL-60 Cells (Table 1)

The measurement of differentiation in HL-60 cells (human leukemia cells) was carried out according to the general procedures described by DeLuca et al., U.S. Pat. No. 4,717,721. In addition to the methods described therein, nonspecific acid esterase activity was measured as described by the kit marketed by the Sigma Chemical Corporation of St. Louis, Mo. As shown in Table 1, degree of differentiation is assessed by three different assays (NBT reduction, phagocytosis, and esterase activity) and results are expressed as the percent of differentiated cells produced in response to treatment with various concentrations of vitamin D compounds.

TABLE 1

Differentiation Activity of 24-Dihomo-1,25-$(OH)_2D_3$ in HL-60 Cells in Culture

| Compound | Concentration (molar) | % Cells Showing Differentiation | | |
|---|---|---|---|---|
| | | NBT Reduction | Phago- cytosis | Esterase |
| 1,25-$(OH)_2D_3$ | $1 \times 10^{-9}$ | $32 \pm 3^a$ | $28 \pm 3^a$ | $28 \pm 2^a$ |
| | $1 \times 10^{-8}$ | $51 \pm 3$ | $56 \pm 3$ | $60 \pm 4$ |
| | $1 \times 10^{-7}$ | $82 \pm 4$ | $84 \pm 4$ | $86 \pm 2$ |
| 24-Dihomo- 1,25-$(OH)_2D_3$ (compound 32) | $1 \times 10^{-9}$ | $28 \pm 3$ | $36 \pm 3$ | $35 \pm 4$ |
| | $5 \times 10^{-9}$ | $64 \pm 4$ | $62 \pm 4$ | $62 \pm 3$ |
| | $1 \times 10^{-8}$ | $70 \pm 2$ | $68 \pm 2$ | $68 \pm 4$ |
| | $5 \times 10^{-8}$ | $93 \pm 5$ | $94 \pm 2$ | $94 \pm 2$ |

$^a$Standard error of the mean of 3–4 determinations.

The results of these three assays are shown in Table 1. It is evident that the novel homolog 24-dihomo-1,25-$(OH)_2D_3$ (compound 32) is much more active than 1,25-$(OH)_2D_3$ itself in causing differentiation of HL-60 cells in culture (Table 1). Thus, 1,25-$(OH)_2D_3$, the natural hormone, induces the differentiation of about 50–60% of the cells at a concentration of $1 \times 10^{-8}$ molar, whereas the new 24-dihomo analog (compound 32) gives over 60% differentiation at five-fold lower concentration ($5 \times 10^{-9}$M). Similarly, a concentration of $1 \times 10^{-7}$ molar is required for 1,25-$(OH)_2D_3$ to produce about 80% differentiated cells, but the dihomo analog gives better than 90% differentiation at $5 \times 10^{-8}$M (e.g. 5x lower). These results strongly support the conclusion that the 24-dihomo-1,25-$(OH)_2D_3$ is 5–10 times more active than 1,25-$(OH)_2D_3$ in causing differentiation of HL-60 cells in culture.

EXAMPLE 6

Assay for calcemic activity in the rat (a) Intestinal Calcium Transport Activity and Mineralization of Rachitic Rat Bone (Table 2)

Male weanling rats were obtained from the Harlan-Sprague Dawley Company of Madison, Wis. and fed the high calcium, low phosphorus rachitogenic diet described by Suda et al. (J. Nutr. 100, 1049–1052, 1970). They were fed on this diet for a total of 4 weeks ad libitum. At the end of the third week the animals were divided into groups of 6 rats each. One group received a daily injection of vehicle (0.1 ml of 95% propylene glycol, 5% ethanol) interperitoneally. The remaining groups received the same amount of vehicle but containing one of the following doses: 12.5 ng 1,25-$(OH)_2D_3$; 25 ng 1,25-$(OH)_2D_3$; 12.5 ng 24-dihomo-1,25-$(OH)_2D_3$; or 25 ng 24-dihomo-1,25-$(OH)_2D_3$. The animals were killed 24 hours after the last dose, the intestines removed, and the duodenal segments were used to measure intestinal calcium transport as described by Halloran and DeLuca (*Arch. Biochem. Biophys.* 208, 477–486, 1981). Calcium transport activity is presented in Table 2 as the calcium transport ratio, indicated by an I/O notation [the concentration of calcium in the serosal medium (I) over the calcium concentration in the mucosal medium (0)]. To assay mineralization of bone in response to test compounds, the femurs of all animals were removed, extracted for 24 hours with 95% ethanol in a Soxlet extractor and 24 hours with chloroform using a Soxhlet extractor. They were dried to constant weight and the total as well as percent ash determined in the femurs following ashing at 600° F. for 24 hours. The calcium transport ratio is indicated by an I/O notation [the concentration of calcium in the serosal medium (I) over the calcium concentration in the mucosal medium (0)]. The ash content is measured in total milligrams of ash/femur or the percent ash based on a defatted dry bone weight.

TABLE 2

Response of Rachitic Rats to 24-Dihomo-1,25-Dihydroxyvitamin $D_3$

| Group | Calcium Transport Ratio I/O (mean ± S.E.M.) | Femur Ash mg (mean ± S.E.M.) | Femur Ash % (mean ± S.E.M.) |
|---|---|---|---|
| Control (Vehicle) | $4.0 \pm 0.2^a$ | $17.7 \pm 1.0^a$ | $14.0 \pm 0.20^a$ |
| 1,25-$(OH)_2D_3$ | | | |
| 12.5 ng/day | $10.4 \pm 0.8$ | $26.3 \pm 1.6$ | $18.9 \pm 0.52$ |
| 25 ng/day | $13.2 \pm 1.0$ | $26.4 \pm 1.7$ | $19.9 \pm 1.3$ |
| 24-Dihomo- 1,25-$(OH)_2D_3$ (compound 32) | | | |
| 12.5 ng/day | $3.0 \pm 0.3$ | $21.0 \pm 1.0$ | $14.75 \pm 1.4$ |
| 25 ng/day | $3.0 \pm 0.4$ | $18.7 \pm 1.5$ | $14.8 \pm 0.69$ |

$^a$Standard error of the mean of 6 determinations.

(b) Measurement of Intestinal Calcium Transport and Bone Calcium Mobilization (Tables 3 and 4)

Male weanling rats were obtained from the Harlan Sprague Dawley Company and fed the low calcium vitamin D-deficient diet described by Suda et al. (J. Nutr. 100, 1049–1052, 1970) for a period of 4 weeks. At the end of the third week the animals received the indicated doses (Tables 3 and 4) dissolved in 95% propylene glycol and 5% ethanol. Each animal received 0.1 ml of solvent vehicle containing the indicated dosage each day for 7 days; the control group received solvent only. Intestinal calcium transport was measured as described by Halloran and DeLuca (*Arch. Biochem. Biophys.* 208, 477–486, 1981) and serum calcium was measured using an atomic absorption spectrophotometer (U.S. Pat. No. 4,717,721).

TABLE 3

Response of Rats on a Low Calcium Diet to 24-Dihomo-1,25-Dihydroxyvitamin $D_3$

| Group | Calcium Transport I/O (mean ± S.E.M.) | Serum Calcium mg % (mean ± S.E.M.) |
| --- | --- | --- |
| Control | 4.8 ± 0.26[a] | 4.1 ± 0.05[a] |
| 1,25-$(OH)_2D_3$ | | |
| 12.5 ng/day | 11.2 ± 0.6 | 4.8 ± 0.08 |
| 25 ng/day | 13.2 ± 1.2 | 4.8 ± 0.08 |
| 24-Dihomo-1,25-$(OH)_2D_3$ (compound 32) | | |
| 125 ng/day | 9.4 ± 0.8 | 4.2 ± 0.06 |

[a]Standard error of the mean of 6 determinations.

TABLE 4

Response of Serum Calcium of Vitamin D-Deficient Rats on a Low Calcium Diet to 24-Dihomo-1,25-Dihydroxyvitamin $D_3$

| Group | Serum Calcium mg % (mean ± S.E.M.) |
| --- | --- |
| Control | 3.4 ± 0.07[a] |
| 1,25-$(OH)_2D_3$ | |
| 12.5 ng/day/7 days | 3.7 ± 0.17 |
| 25 ng/day | 4.1 ± 0.07 |
| 75 ng/day | 4.6 ± 0.09 |
| 24-Dihomo-1,25-$(OH)_2D_3$ (compound 32) | |
| 25 ng/day | 3.6 ± 0.16 |
| 125 ng/day | 3.95 ± 0.13 |
| 250 ng/day | 3.80 ± 0.05 |

[a]Standard error of the mean of 6 determinations.

The results shown in Tables 2 and 3 illustrate that 24-dihomo-1,25-$(OH)_2D_3$ (compound 32) is much less active than 1,25-$(OH)_2D_3$ in stimulating intestinal calcium transport. 1,25-$(OH)_2D_3$ achieves maximal calcium transport at between 12.5 and 25 ng per day, whereas 24-dihomo-1,25-$(OH)_2D_3$ showed no activity whatever at these doses (Table 2), and did produce a significant response only at the 125 ng per day level (Table 3). Even then, the response was lower than that produced by 1,25-$(OH)_2D_3$ at 12.5 ng/day. These results show the dihomo analog to have one-tenth or less of the activity of 1,25-$(OH)_2D_3$ in stimulating intestinal calcium transport (Tables 2 and 3).

In the case of bone mineralization (Table 2), a similar lack of effectiveness of 24-dihomo-1,25-$(OH)_2D_3$ on mineralization of the skeleton is observed. The entries under Femur Ash and Femur Ash % in Table 2 show that doses of 12.5 and 25 ng of the dihomo compound (32) produce no significant change compared to the control, whereas 1,25-$(OH)_2D_3$ elicits significant mineralization at these same dosage levels.

When bone calcium mobilization (serum calcium levels) was measured, it is clear that 1,25-$(OH)_2D_3$ produced a significant elevation of serum calcium at the expense of bone at doses of 12.5 and at 25 ng per day (Tables 3 and 4). In contrast, 24-dihomo-1,25-$(OH)_2D_3$ elicited no significant response at a dosage level of 25 ng/day and none at 125 ng/day in one experiment (Table 3), and a very modest rise in serum calcium when administered at levels of 125 and 250 ng/day in a second experiment (Table 4). Notable, too, is the observation (Table 4) that increasing the dose from 125 to 250 ng/day does not further increase blood calcium levels. These results indicate that the 24,24-dihomo-1,25-$(OH)_2D_3$ is less than one-tenth as active as 1,25-$(OH)_2D_3$ in raising serum calcium at the expense of bone. These results are confirmed also by a third experiment measuring bone calcium mobilization, in which the dihomo analog 32 when tested over a dosage range up to 1000 ng/day elicited no response.

Thus, it is evident that the new vitamin D homolog (compound 32) shows unexpected preferential activity in cellular differentiation while having little effect on calcium transport and mobilization. This is the type of activity pattern desired for a vitamin D compound intended for use as an anticancer agent. By virtue of its very low calcemic action (compared to 1,25-$(OH)_2D_3$), the new dihomo-1,25-$(OH)_2D_3$ analog can be administered without inducing an undesired hypercalcemic response in patients, while exhibiting a potency even higher than that of 1,25-$(OH)_2D_3$ in arresting malignant cell proliferation and in inducing cell differentiation. The same type of activity pattern, namely pronounced differentiation activity combined with very low or abolished calcemic potency, can be expected for the 24-trihomo analog of this invention, which compound, therefore, will also exhibit a greatly enhanced and advantageous differentiation/calcemic activity ratio. Although structurally related to 24-homo-vitamin D analogs of the prior art (U.S. Pat. No. 4,717,721), the side chain homovitamin D compounds of this invention present a radically altered activity profile: high activity in cell differentiation combined with nearly abolished calcemic potency. Furthermore, since the differentiation activity is expressed in the case of human leukemia cells (HL-60 cells), it is clear that these new vitamin homologs can be used for the treatment of malignancies in humans, specifically leukemias.

For treatment purposes, these compounds can be formulated as solutions in innocuous solvents, or as emulsions, suspensions or dispersions in suitable and innocuous solvents or carriers, or as pills, tablets or capsules by conventional methods known in the art. Such formulations may also contain other pharmaceutically-acceptable and non-toxic excipients, such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal. For the treatment of human leukemia, the homovitamin D compounds of this invention are administered to subjects in dosages sufficient to induce the differentiation of leukemic cells to macrophages. Preferred dosage amounts are from 0.5 μg to 50 μg per day, it being understood that dosages can be adjusted to still higher levels depending on the severity of the disease or the response or the condition of subject as well-understood in the art.

We claim:

1. A process for the preparation of vitamin D compounds having the general structure:

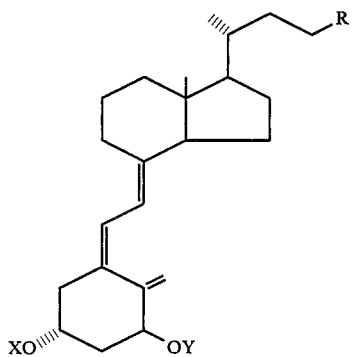

where X and Y, which may be the same or different, are selected from the group consisting of hydrogen and a hydroxy-protecting group, and where R is selected from the group consisting of alkyl, fluoro-substituted alkyl, hydroxy-substituted alkyl, hydroxy and fluoro-substituted alkyl, hydroxy-protected hydroxy-substituted alkyl and hydroxy-protected hydroxy- and fluoro-substituted alkyl, which comprises treating a vitamin D-22-tosylate derivative, of the general structure:

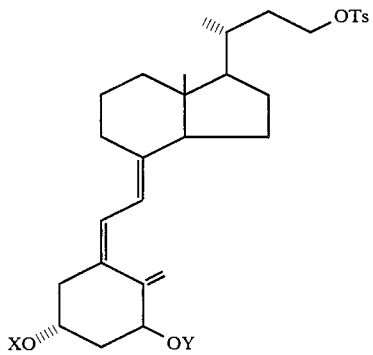

where X and Y are selected from the group consisting of hydrogen and hydroxy-protecting groups, with an alkylphenylsulfone derivative of the general structure:

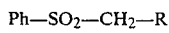

Ph—SO$_2$—CH$_2$—R wherein R is selected from the group consisting of alkyl, fluoro-substituted alkyl, hydroxy-substituted alkyl, and hydroxy- and fluoro-substituted alkyl, any hydroxy group present being preferably derivatized by hydroxy-protecting groups, thereby obtaining a side chain sulfone adduct, having the following general structure:

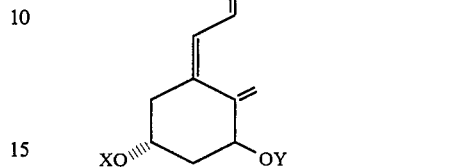

wherein X, Y and R represent the groupings defined above, and reductively desulfonating said side chain sulfone adduct so as to obtain the corresponding vitamin D compound, and, optionally removing the hydroxy-protecting groups present.

2. The method of claim 1 where X and Y are hydroxy-protecting groups.

3. The method of claim 2 where R is 4-methyl-4-hydroxypentyl in hydroxy-protected form.

4. The method of claim 2 where R is 5-methyl-5-hydroxyhexyl in hydroxy-protected form.

5. Compounds having the structure:

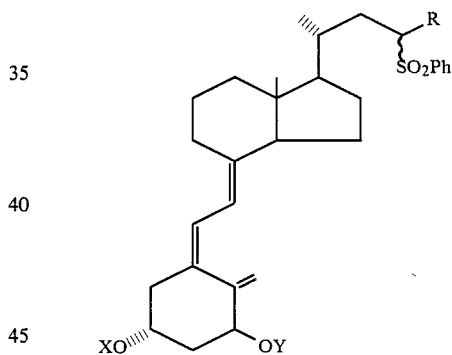

wherein X and Y, which may be the same or different, are selected from the group consisting of hydrogen and a hydroxy-protecting group, and where R is selected from the group consisting of 4-methyl-4-hydroxy-pentyl, 5-methyl-5-hydroxy-hexyl, and their corresponding hydroxy-protected forms.

6. The compounds of claim 5 where X and Y are hydrogen.

7. The compounds of claim 5 where X and Y are hydroxy-protecting groups.

8. The compounds of claim 5 where R is 4-methyl-4-hydroxypentyl.

9. The compounds of claim 5 where R is 4-methyl-4-hydroxypentyl in its hydroxy-protected form.

10. The compounds of claim 5 where R is 5-methyl-5-hydroxyhexyl.

11. The compounds of claim 5 where R is 5-methyl-5-hydroxyhexyl in its hydroxy-protected form.

12. Compounds having the structure:

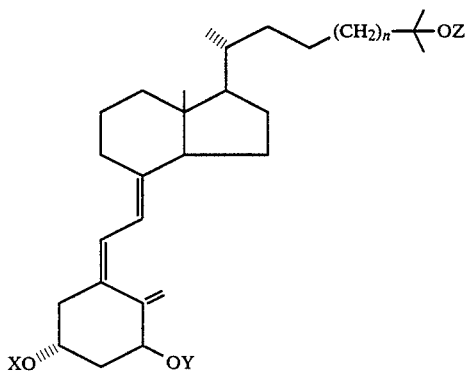

where X, Y and Z, which may be the same or different, selected from the group consisting of hydrogen and a hydroxy-protecting group, and where n is 3 or 4.

13. The compounds of claim 12 where X, Y and Z are hydroxy-protecting groups.

14. The compounds of claim 13 where X, Y and Z are alkylsilyl groups.

15. The compounds of claim 12 where X, Y and Z are hydrogen.

16. A pharmaceutical composition containing a compound as claimed in claim 12 together with a pharmaceutically acceptable excipient.

17. A pharmaceutical composition as claimed in claim 16 where the compound is 24-dihomo-1α,25-dihydroxyvitamin $D_3$.

18. A pharmaceutical composition as claimed in claim 16 where the compound is 24-trihomo-1α,25-dihydroxyvitamin $D_3$.

19. A method for inducing and enhancing cell differentiation in malignant cells which comprises exposing said cells to at least one of the compounds claimed in claim 12, in an amount sufficient to induce cell differentiation.

20. The method as claimed in claim 19, where the compound is 24-dihomo-1α,25-dihydroxyvitamin $D_3$.

21. The method as claimed in claim 19 where the compound is 24-trihomo-1α,25-dihydroxyvitamin $D_3$.

22. A method for treating neoplastic diseases which comprises administering to a subject having a neoplastic disease an effective amount of at least one of the compounds of claim 12.

23. The method of claim 22 where the compound administered is 24-dihomo-1α,25-dihydroxyvitamin $D_3$.

24. The method of claim 22 where the compound administered is 24-trihomo-1α,25-dihydroxyvitamin $D_3$.

25. 24-dihomo-1α,25-dihydroxyvitamin $D_3$.

26. 24-trihomo-1α,25-dihydroxyvitamin $D_3$.

* * * * *

UNITED STATES PATENT AND TRADEMARK OFFICE
CERTIFICATE OF CORRECTION

PATENT NO. : 4,927,815

DATED : May 22, 1990

INVENTOR(S) : Hector F. DeLuca et al

It is certified that error appears in the above-identified patent and that said Letters Patent is hereby corrected as shown below:

Col. 20, Line 60, delete "hydroxypentyl" and substitute therefore --- hydroxy-pentyl ---; Col. 20, Line 62, delete "hydroxypentyl" and substitute therefore --- hydroxy-pentyl ---; Col. 20, Line 64, delete "hydroxyhexyl" and substitute therefore --- hydroxy-hexyl ---; Col. 20, Line 67, delete "hydroxyhexyl" and substitute therefore --- hydroxy-hexyl---.

Signed and Sealed this

Second Day of July, 1991

Attest:

HARRY F. MANBECK, JR.

*Attesting Officer*　　　　*Commissioner of Patents and Trademarks*